United States Patent
Mohanty et al.

(10) Patent No.: US 11,658,514 B1
(45) Date of Patent: May 23, 2023

(54) WIRELESS CHARGING OF SENSOR DEVICE FOR DIAGNOSIS AND MONITORING

(71) Applicant: FemtoDx, Inc., Beverly Hills, CA (US)

(72) Inventors: Pritiraj Mohanty, Beverly Hills, CA (US); Shyamsunder Erramilli, Quincy, MA (US)

(73) Assignee: FemtoDx, Inc., Beverly Hills, CA (US)

( * ) Notice: Subject to any disclaimer, the term of this patent is extended or adjusted under 35 U.S.C. 154(b) by 208 days.

(21) Appl. No.: 15/676,847

(22) Filed: Aug. 14, 2017

Related U.S. Application Data

(60) Provisional application No. 62/374,320, filed on Aug. 12, 2016.

(51) Int. Cl.
| | |
|---|---|
| *H02J 50/00* | (2016.01) |
| *H02J 7/02* | (2016.01) |
| *A61B 5/145* | (2006.01) |
| *A61M 31/00* | (2006.01) |
| *A61N 5/02* | (2006.01) |
| *A61N 5/04* | (2006.01) |
| *A61B 5/07* | (2006.01) |
| *H02J 50/20* | (2016.01) |
| *H02J 50/12* | (2016.01) |
| *A61B 1/06* | (2006.01) |
| *A61B 5/24* | (2021.01) |
| *H04B 1/3827* | (2015.01) |
| *H02J 7/34* | (2006.01) |
| *H01Q 1/27* | (2006.01) |

(52) U.S. Cl.
CPC ............ *H02J 7/025* (2013.01); *A61B 1/0684* (2013.01); *A61B 5/076* (2013.01); *A61B 5/14503* (2013.01); *A61B 5/24* (2021.01); *A61M 31/002* (2013.01); *A61N 5/022* (2013.01); *A61N 5/045* (2013.01); *H02J 50/12* (2016.02); *H02J 50/20* (2016.02); *A61B 2560/0219* (2013.01); *A61M 2205/3523* (2013.01); *A61M 2205/8243* (2013.01); *H01Q 1/273* (2013.01); *H02J 7/345* (2013.01); *H04B 1/385* (2013.01)

(58) Field of Classification Search
CPC . H02J 7/025; H02J 50/12; H02J 50/20; A61B 1/0684; A61B 5/14532; A61B 5/076; A61B 5/24
See application file for complete search history.

(56) References Cited

U.S. PATENT DOCUMENTS

2015/0057496 A1\* 2/2015 Schatz ............... A61B 1/00029
600/102

\* cited by examiner

*Primary Examiner* — Marjan Fardanesh
(74) *Attorney, Agent, or Firm* — Wolf, Greenfield & Sacks, P.C.

(57) ABSTRACT

This application describes a novel approach of wireless charging or powering of a sensor-based device used for in vivo diagnosis and monitoring. In addition to implantable or subcutaneous devices, this approach can also be used for wireless charging of wearable and handheld devices. Specifically, this application describes charging of diagnostic and monitoring devices used for disease detection and management. More specifically, this application describes a method to wirelessly power integrated devices designed to detect or monitor analytes (e.g. biological or chemical species) and release drugs into the body in response to a specific change in the body's vitals, detected by the device.

16 Claims, 7 Drawing Sheets

WIRELESS CHARGING OF SENSOR DEVICE FOR DIAGNOSIS AND MONITORING

RELATED APPLICATIONS

This application claims priority to U.S. Provisional Application No. 62/374,320 filed Aug. 12, 2016, which is incorporated herein by reference in its entirety.

BACKGROUND

Figure 1:
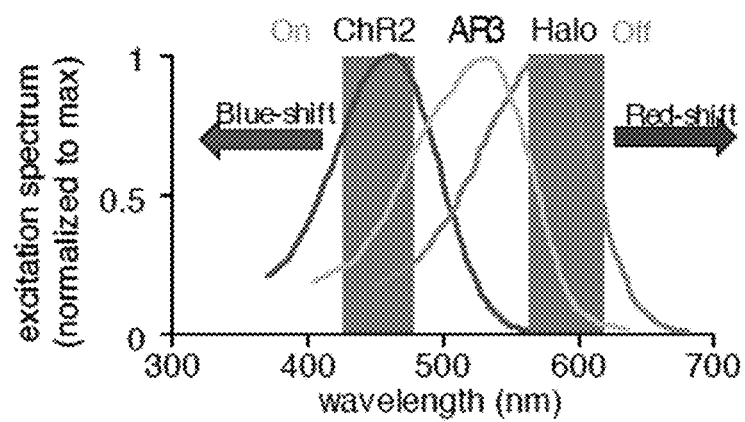
FIG. 1. Excitation spectrum of optogenetic rhodopsins to activate (on) or silence (off).
Figure 2:
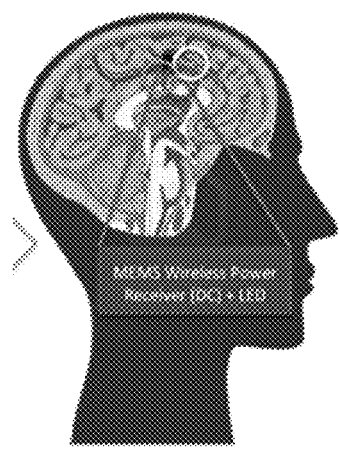
FIG. 2. Current state-of-the-art research in optogenetics involves animal (mouse) models, where activation of light-sensitive proteins is achieved by fiber-optic cables, typically carrying single wavelength lights. The approach discussed here in this application will help replace wires and fiber optic cables by an implantable miniature wireless powering device, designed for a human brain and tested in a simulated tissue environment or a phantom, and eventually in a human brain.
Figure 3:
FIG. 3. Wireless powering system block diagram.
Figure 4:
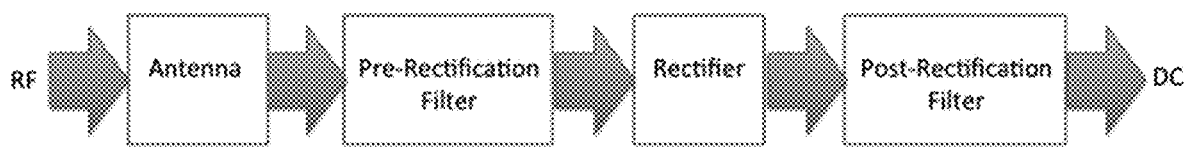
FIG. 4. Wireless power receiving system block diagram.

Implantable devices are devices that are implanted in the human body to extend and improve quality of life, addressing a wide range of medical problems. According to some estimates, these devices account for over $200 billion in revenue worldwide and over $85 billion in revenue in US, annually. In addition to an exploding number of implantable devices being sold every year, the number of corresponding procedures being performed to implant a new device or correct or manage an implantable device is growing at a fast pace. A huge fraction of the procedures involves follow-up or corrective procedures to replace or correct an implantable device.

Implantable devices can be divided into two categories: (i) active and (ii) passive. Active devices are those that require power to operate. A classic example of an active implantable device is a cardioverter defibrillator. A passive device is one that does not require any power or energy to operate. Examples include prosthetics, stents and tubes in the heart to lenses in the eye and tubes in the ear. This application is focused on active devices that require power to operate, and that must be charged periodically.

Apart from the existing implantable devices, there are two new classes of implantable devices that can tremendously benefit from a wireless charging mechanism. These are optogenetic devices, implanted in the brain and diagnostic and monitoring devices implanted in the body for detecting biological or chemical analytes for disease diagnosis or monitoring.

One prominent example of an active implantable device is a remotely powered device in the human (or mammalian) brain to activate embedded light emitting diodes or other light generating mechanisms to control and manipulate brain activity with light of specific wavelength. This field is termed optogenetics. In order to transport light into a mammalian brain though the skull, existing methods require the use of fiber optics coupled to an external LED (light emitting diode) source, with holes drilled through the skullcap. In principle, light sources could be embedded underneath the skullcap, but need to be activated by an external power source with wires. Here, this application describes an ultra-compact wireless power source capable of generating at least 0.1-10 mW of power for controlling three different LEDs on and off for both neuronal activation and silencing.

At present, the challenges for such implantable device applications are several. The most important are: (i) While providing sufficient power to drive embedded LEDs, the intensity of the microwave radiation needs to be low, consistent with guidelines that establish SAR (Specific Absorption Rate) level limit of 3.2 W/kg; (ii) The wireless power device needs to be biocompatible, and compact, with a specific mass of 1 mg/W. At present there is no existing technology or instrumentation that can wirelessly power an embedded LED source consistent with these limitations.

A compact, wireless power device for activating embedded LED sources will have widespread impact. A rapidly growing list of potential biomedical applications includes (i) unraveling the connectome in the brain (ii) restoring neuronal activity in patients with a range of neurological disorders including traumatic brain injury, stroke, Parkinson's and Alzheimer's and others.

SUMMARY

An implantable device and related methods are described herein.

In one aspect, an implantable device is provided. The device comprises a resonator and is configured to receive electromagnetic radiation.

In one aspect, an implantable device is provided. The device comprises a resonator and is configured to measure an electrical response from a neuron or a nerve.

In one aspect, an implantable device is provided. The device comprises a resonator and is configured to detect a signal representing the presence of an analyte.

DESCRIPTION

An implantable diagnostic device is embedded inside the body for diagnosis or monitoring. A standard example is a continuous glucose monitoring device that detects glucose in blood, tear or interstitial fluid. Such a device could be enhanced for long-term operation if it could be charged wirelessly to operate the sensor system in the implantable device. Furthermore, such a monitoring device could be enhanced by integrating it with a drug delivery system for remote release of the appropriate drug into the body in response to specific indication of the body's vitals. For instance, an implantable glucose monitoring device could contain an insulin delivery module that can release insulin into the bloodstream depending on the blood sugar level.

In another configuration as a subcutaneous device, an implantable sensor device can be located on the skin or under the skin. In certain applications, the device can be embedded under the skin or applied as a patch. The sensor can access a range of analytes in this configuration. These analytes can be detected in blood vessels and nerves in the dermis. The sensor can be configured to detect markers for diagnosis or monitoring of specific diseases. In yet another configuration, the implantable sensor can be used as a wearable device. Examples of this include arm and leg bracelets, earrings and other wearable configurations on the body. In one variation, the device can be worn as a wristwatch, and fluid sample from the body such as a drop of blood can be applied to an exposed surface of the device, which will sense the desired analyte in the fluid sample. In another variation, it is possible to connect a disposable cartridge, which can be plugged into the device. The cartridge will contain the appropriate fluid sample to be tested. In all these configurations, semiconductor nanosensors can be used for the detection of the analytes.

Wireless charging of these devices is paramount to the long-term operation of these devices, and for ease of use necessary for adoption.

The current technology for optogentics applications involves a wired solution, where fiber optic cables connect to the LED source through the skullcap. This application describes a wireless solution, which can be left inside the mammalian/human brain or the human body as an implant. This device can be powered wirelessly on an as-needed basis.

There are many wireless powering solutions. None of these can be used in a neurological or in vivo diagnostics application, as they are not designed for the right power output; they are not designed to operate in a tissue environment; and they are not designed to be biocompatible—i.e. packaging material in these devices could cause local inflammation and cell damage. These technologies/instrumentations are briefly described below.

i) RFID: Radio Frequency Identification is a system, designed to carry data in suitable transponders, and retrieve those data in machine-readable form. Data within a tag may provide identification for an item in manufacture, goods in transit, a location, a vehicle, an animal or an individual. A system requires, in addition to tags, "readers" for interrogating the tags and some means of communicating the data to a host computer or information management system. These are wireless data transfer systems, operating at high MHz (megahertz) or microwave (2.45 GHz (Gigahertz) or 5.8 GHz for road tolling) frequencies, and low power levels (less than a few microwatt). They cannot be used for high power transfer to power LEDs, requiring powers of at least 3 orders of magnitude more than what the active RFIDs use. Electronic Article Surveillance (EAS) systems are similar to RFIDs.

ii) Wireless transport of electrical energy by magnetic induction is achieved in a number of consumer electronic devices. Devices such as smart phones, laptops and other communication devices can be wirelessly charged by being placed on a charging station, even inside a car. This technology of magnetic induction has been around for over 100 years, as first demonstrated by Tesla, and, more recently, by the MIT media lab. Wireless powering of devices implanted inside a mammalian brain cannot use near-field 60-Hz magnetic induction, as the induction coil sizes tend to be much larger. Second, large magnetic fields close to the brain can produce serious undesirable effects. Similar problems arise for implantable devices used for in vivo diagnostics and monitoring.

iii) Wireless transport of electrical energy by microwave radiation has been proposed for large scale power stations on earth using high power (>1 GW) microwave radiation from solar powered satellites. The frequencies of choice are 2.45 GHz and 5.8 GHz, same as that of the RFID systems. They also suffer from similar issues as RFID, as outlined above.

iv) Wireless transport of electrical energy by microwave radiation has been recently demonstrated in implantable devices. These include ocular implants and cardiovascular pressure monitors integrated with stents. These seminal works demonstrate that it is possible to wirelessly power implantable devices through tissue. However, these devices were specifically designed for ocular implants in the eye, where the size and the nature of the tissue materials are very different from that of a mammalian brain. The power transfer efficiency is shown to be as large as 12% at an input power of 1 W with a reduction of up to 4 dB in the in vivo state inside the tissue. This is truly the state-of-the-art in the field of wireless powering of implantable devices. However, these devices cannot be used for optogenetics applications inside a mammalian brain or the human body for a number of reasons. The length of propagation in a human brain is substantially larger and the tissue environment is fundamentally different.

Implantable devices that require power to operate can be powered wirelessly without any wiring or contact. In some cases, it is necessary, as for optogenetics applications described below. In some cases, it enables the device to operate for a longer time without any interruption. For applications such as continuous glucose monitoring, the ability to charge the device wirelessly could enable widespread adoption. In the following, two applications are described in detail: (i) optogenetics, (ii) in vivo diagnostics.

Optogenetics involves the use of microbial opsins that can be activated by visible light to manipulate cells with high specificity and temporal precision even inside intact tissue or behaving animals. The proposed device will extend the related tools by replacing optical fibers with an implanted device that can be excited wirelessly. With the use of a miniaturized implantable wireless device, current optogenetics approaches can be extended to the studies in a human brain of the neural circuits underlying brain diseases and symptoms relevant to fear, anxiety, depression, schizophrenia, addiction, Parkinson's disease, epilepsy and Alzheimer's disease. For instance, a recent study demonstrated that by optogenetics stimulation (with channelrhodopsin) acute activation of neuron axon terminals can produce an anxiolytic effect. Similar studies have been done on Parkinson's neural circuit.

The field of optogenetics started with the demonstration that certain microbial rhodopsins can be heterologously expressed in mammalian neurons, with action potentials that can be triggered with light due to the transport of ions by the photoactive algal membrane protein channel rhodoposin. Although the field is only about 8 years old, the field has since exploded, even more so after the breakthrough observation that neurons can also be silenced by the incorporation of archaerhodopsin. Three main classes of microbial rhodopsins—channelrhodopsins (ChR), halorhodopsins (HR), and archaerhodopsins (AR3 and ArchT)—are especially useful for optogenetics because they act to depolarize or hyperpolarize the neuronal cell membrane. Each class of rhodopsin has a slightly different wavelength of absorption (FIG. 1) that can then be selectively excited by different LEDs.

The wireless powering approach, described here, will output enough DC power to run three LEDs at the same time, enabling multiple light-sensitive proteins at the same time for the study of complex pathways and activity patterns in neural circuits. ChR2 channelrhodopsin allows positive sodium ion to pass in response to blue light at near the maximum wavelength of absorption of $\lambda_{max}$~470 nm. VChR1 channelrhodopsin responds to some wavelengths of green and yellow light at 535 nm and 589 nm. Native AR3, and the closely related protein ArchT with $\lambda_{max}$~565 nm is the preferred optogenetic tool for silencing neurons. NpHR halorhodopsin regulates the flow of negative chloride ions in response to yellow light with $\lambda_{max}$~589 nm. The red-shifted maximum in halorhodopsins makes them attractive due to reduced overlap with ChR (see FIG. 1).

Up to now, all optogenetic studies have been done on mice. The approach, described here, followed by integrated testing in a simulated tissue environment (tissue phantom), will enable the first optogenetic studies in a human brain.

In addition to enabling the first human studies of optogenetics, this device can address numerous non-neuroscience problems that require remote powering of miniaturized sensor-based devices. In particular, semiconductor-based nanowire sensors could be ideal because of the small overall size of the sensor chip. The in vivo applications include pressure monitoring in the heart, blood flow monitoring, cardioverter defibrillator, glucose monitoring et cetera. A second set of applications includes disease screening, diagnosis, staging and monitoring by implantable devices that detect markers and analytes.

This application is focused on the design of a miniaturized receiver circuit, encapsulated in a biocompatible package or a wafer-level package (co-packaged with a semiconductor-based sensor chip), capable of generating enough DC power. For optogenetics applications, the required DC power is typically >1 mW to operate three LEDs. For diagnostics applications, the power required could range from 1 microwatt-1 watt, depending on the number of sensors and the degree of multiplexing.

For an integrated wireless power receiver circuit module, it is possible to use inductive powering using magnetic fields, RF (radio frequency) powering using a resonant circuit such as a micromechanical resonator, LC resonator or SRR (split-ring resonator). Other types of resonant circuits may also be used. In the following, without loss of generality, a couple of such approaches are described.

The first fundamental consideration involves the choice between two basic methods of wireless powering: low frequency inductive powering using magnetic fields and high frequency RF powering using a receiver antenna/rectifier system to collect RF power and convert it to DC power. Low frequency inductive powering uses magnetic field coupling between a primary and a secondary coil, one of which is embedded in the implant, and the other is a part of the remote powering subsystem or RF powering module. A fundamental limitation is the need for proximity and alignment required for better coupling. Remote powering based on electromagnetic wave propagation at microwave frequencies (typically GHz) allows greater transfer distances and immunity to alignment.

A further advantage of higher frequency is the size reduction of the receiver, which leads to miniaturization of the overall device. A smaller device size is of tremendous interest for biomedical implants for the brain and the heart, because of the physical size of the part of these organs being probed. For instance, pressure monitors in the heart need to be small for integration with stents or insertion in the heart's chambers or in the pulmonary artery.

A full overview of the wireless powering system based on high frequency RF transmission is shown below. It can comprise an external microwave power source or transmitter, containing a transmitter antenna. The electromagnetic wave from the transmitter passes through free space wirelessly and reaches the receiver. The receiver circuit contains a receiver antenna to collect the RF power and a rectifier circuit to convert the RF power to DC power.

There is a fundamental difference between a conventional wireless powering device and the device configuration described here. In implantable device configuration, wireless transfer of power must occur partly through free space and partly through tissue.

For specific neuroscience applications such as optogenetics and in vivo diagnostics, the device must be designed to account for absorption of RF radiation through bone, skin, tissue and blood. Fortunately, advanced simulation packages (like Ansoft) contain human body models to simulate propagation of electromagnetic wave through layers of biomaterials such as skin, bone, tissue and blood, all of which have very different absorption and transmission characteristics. An additional consideration is the local heating in the tissue material due to microwave absorption, since heating of the experimental region due to RF (microwave) power transmission can fundamentally change the characteristics of the proteins or cells being studied.

The antenna is needed to collect the RF power and transfer the energy to the pre-rectification filter. The pre-rectification filter is a band-pass filter centered at the frequency of operation, and is needed to collect power only within the desired frequency band. An additional function of the pre-rectification filter is to avoid unwanted higher harmonics of the signal produced by the nonlinear I-V characteristics of the diodes in the rectifier. The rectifier is fundamental to the system as it converts RF power into DC power. It usually comprises a network of diodes with high switching speed. Other important considerations for the diodes are high power handling, I-V characteristics, breakdown voltage, forward bias voltage and saturation current. The post-rectification filter is usually a low-pass filter, allowing only a signal below a certain set frequency to pass. It prevents the appearance of any signal components of unwanted frequencies or higher harmonics. Finally, the DC power can be used to directly power a device such as an LED or to store the power in a battery, usually achieved by storing the charge in a capacitor.

In the following, system requirements in terms of the important parameters such as frequency of operation, input and output power levels, size and packaging considerations are described.

i) Operation Frequency: As described earlier, wireless powering by RF or electromagnetic wave is fundamentally more efficient. It has basic advantages over low frequency inductive method, as there is no need for proximity or alignment. Higher frequency operation has additional advantages, which include (a) larger bandwidth for greater instantaneous transfer of information or power, (b) higher frequency resolution for sensing, (c) reduced dimensions for antenna and other components, (d) less interference from nearby applications, (e) fast speed for digital signal processing, (f) less crowded spectrum and (g) difficulty in jamming. The higher the frequency, the smaller is the antenna size. This is the most important consideration; being the largest component in the receiver, antenna size ultimately determines the device size.

The second fundamental consideration is the absorption characteristics of the medium through which the electromagnetic wave has to propagate. The medium comprises free space (air) and biomaterials (skin, bone, tissue and blood). Since the electromagnetic wave needs to propagate through the biomaterial in which the device is embedded, it is also necessary to consider the frequency dependence of penetration depth in body tissue. It is well known that the higher the frequency, the shorter the penetration depth. Hence, the benefits of higher frequency are countered by the fact that the embedded receiver may not receive enough power. The compromise between the effects of higher frequency and penetration depth needs to be explored. Therefore, we propose to explore the 2-6 GHz band. Other practical reasons for choosing this frequency band are the same as those for active RFID tags.

ii) Size: The receiver size of the device is dominated by the size of the antenna, as other components are at least an order of magnitude smaller. As discussed later in the proposal, antenna size will be less than 5 mm×5 mm. Other components described in the block diagram include rectifiers and filters. These components can be easily fabricated using a CMOS process within a die size of 1 mm×1 mm. Even though fabrication of antenna in the same die as the rectifiers and other components seems elegant, it is not necessary for applications in biological research to have a single-die solution as long as the device is fully integrated.

iii) Packaging: Biocompatible hermetic package is necessary to house the device for reliable operation. The package needs to maintain the ambient condition of the device to operate. In addition, it is necessary for the package material to be biocompatible. Moreover, the material should have the least damaging effect on the tissue. A fully packaged device should be ideally less than 8 mm×8 mm×2 mm.

iv) Input and Output Power Levels: Transmit Power: FCC's adopted limit for safe exposure to radio frequency electromagnetic radiation by cellular phones has a SAR (specific absorption rate) level of 1.6 W/kg. Most cellular phones operate at 0.75-1 watt during the talk mode, producing non-ionizing non-heating radiation below the FCC-approved SAR level. Further studies of the effect of millimeter wave on the cells and tissues suggest that 1 watt of power at 2-6 GHz can be used as a safe maximum.

| Wireless Powering Device—Typical System Requirement Dashboard | |
|---|---|
| Frequency | 2-6 GHz |
| Transmit Power | 1 watt at 10 cm distance |
| Converted DC Power | 1 milliwatt |
| DC Voltage | 1.8-2.2 volt |
| DC Current | 500 microampere minimum |
| Size | 8 mm × 8 mm × 4 mm |
| Packaging | Biocompatible, multi-chip-module (MCM) |

The output DC power required to operate three LEDs simultaneously for the proposed experiments in optogenetics is at least 1 mW (at the estimated current level of 250 µA at 2 V). So, the goal is to produce >1 mW of DC power using the device in simulated tissue environment where the transmitter distance is at least 10 cm from the receiver. Similarly for diagnostics applications, power levels of 1 microwatt-1 watt will be required to operate the device in different configurations.

Figure 5:
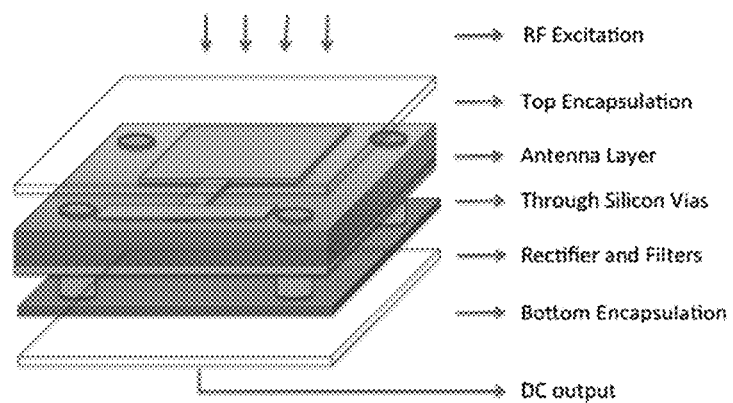
FIG. 5. A system-level schematic of the implantable wireless power receiver device.

The schematic diagram in FIG. 5 shows the breakdown of a wireless power transmission receiver. Since the antenna is the largest component in the receiver, the device is designed to not be larger than the antenna itself. At the top and the bottom are the packaging encapsulation layers. Next layer contains the antenna on a dielectric substrate. The antenna layer has through-silicon-vias (TSV), for making electrical contacts with the next layer, which contains the pre-rectification and post-rectification filters and diodes. The DC output is retrieved through the bottom encapsulation layer at the TSV contact posts, whereas the top layer faces the input radiation or the radio frequency electromagnetic wave.

In the following, the important components such as antenna, matching network, rectifier circuit, switches and packaging are described.

i) Antenna

Figure 6:
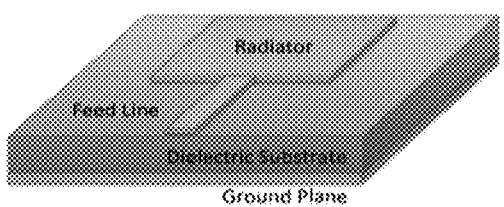
FIG. 6. Layout of a simple patch antenna receiver.

Patch antennas are perfectly suitable for applications where size, mass and profile are critical. They are widely used to deliver wireless capability in aircraft and spacecraft, due to their low weight, conformability and robustness. A patch antenna typically comprises a planar microstrip radiator and a parallel ground plane separated by a dielectric (FIG. 6). Dimensions of the radiator and thickness and dielectric constant of the substrate primarily determine the operation frequency. For many applications, single operation frequency and narrow bandwidth of patch antennas are considered serious limitations. However, for a wireless powering receiver system, these two attributes turn out to be advantages as the frequency of the transmitter and the receiver can be fixed. Narrow bandwidth or higher quality factor is highly desirable as it increases power transfer efficiency.

Frequency of the patch antenna and width of the antenna are related by $$W = \frac{c}{2f_{res}} \sqrt{\frac{2}{\epsilon_r + 1}}$$

where W is the width of the antenna, and c is the speed of light. $\epsilon_r$ is the dielectric constant of the substrate. For a predetermined target frequency, the width W of the antenna can be easily determined.

Free space wavelength $\lambda_0$ and wavelength in the dielectric are related by $\lambda_g = \lambda_0/\sqrt{\epsilon_r}$. An effective dielectric can be defined for W>>h, the thickness of the dielectric substrate:

$$\epsilon_{eff} = \frac{\epsilon_r + 1}{2} + \frac{\epsilon_r - 1}{2}\left(1 + \frac{12h}{W}\right)^{-1/2}$$

The length L can be determined $$L = \frac{c}{2f_{res}\sqrt{\epsilon_{eff}}} - 2\Delta L$$

where $\Delta L$ is a small correction term, called edge extension, which accounts for fringe capacitance.

ii) Matching Network

Figure 7:
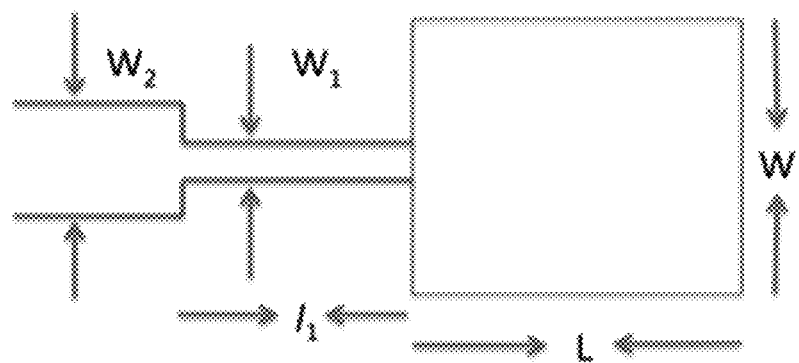
FIG. 7. Schematic diagram of a patch antenna with a microstrip line (with width $W_2$) and a quarter-wavelength transformer (with width $W_1$).
Figure 8:
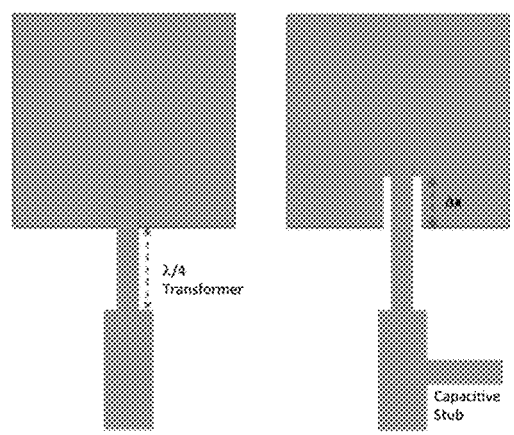
FIG. 8. A patch antenna with a quarter-wavelength transformer (left) and one with a notch impedance network and a reactive capacitive stub (right).

Impedance matching between the antenna radiator/receiver and the feed line can be achieved by a quarter wavelength transformer (FIG. 7). Its dimensions can be determined by $W_1 \sim 0.58$ h and $l_1 = \lambda_g/4$. Input impedance can be found for the condition $W < \lambda_0$:

$$R_{in} = \frac{45 \lambda_0^2}{W^2}$$

The patch antenna can be fed using microstrip-line edge feed (with a microstrip of width $W_2$) as shown in FIG. 5. In addition to the quarter wavelength transformer, used as a matching network, one can additionally tune or modify the impedance by adding a notch (as shown in FIG. 6, where the feed point is recessed by an amount $\Delta x$) or a capacitive stub of length d. Impedance is modified by the notch according to the following relationship:

$$Z(\Delta x) = Z(\Delta x = 0) \cos^2\left(\frac{\pi \cdot \Delta x}{L}\right)$$

and by the capacitive loading stub:

$$Z_{in} = Z_0 (Z_L + i Z_0 \tan(2\pi \lambda/d))(Z_0 + i Z_L \tan(2\pi \lambda/d))^{-1}$$

iii) Antenna Dimensions for 2-6 GHz Band

In the 2-6 GHz band, the optimal patch antenna dimension, roughly the corresponding half wavelength in free space, is in the range of 75-25 mm. This is much larger than the desired device size. The largest dimension of the antenna needs to be less than 4 mm, less than 20% of the half wavelength. The compromise for reduced device size is antenna efficiency. However, it is possible to increase the effective antenna length to match the half wavelength to create standing wave condition. This is done by the so-called "electrical lengthening", where an appropriate inductive load is added to the antenna for impedance matching. Below, we discuss a novel idea of using a micromechanical resonator (MEMS) to provide the required inductive load, necessary to create the resonant condition with a much smaller size.

iv) MEMS Resonant Antenna

Figure 9:
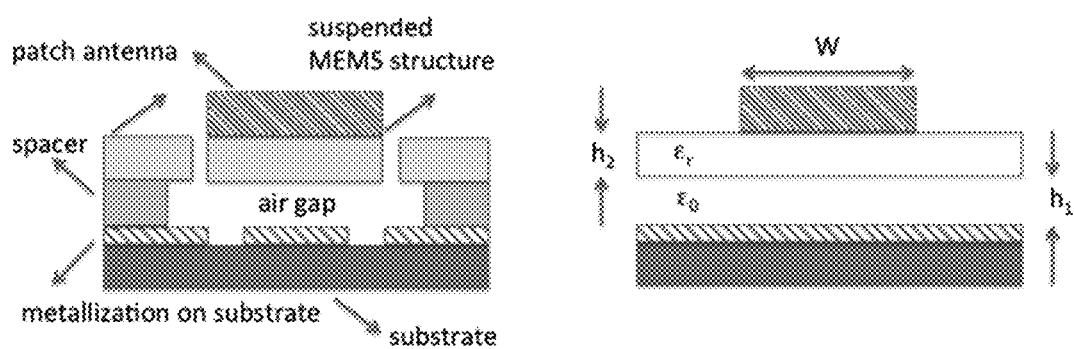
FIG. 9. Cross-sectional view of a MEMS antenna, suspended over an air gap (left). Cross-sectional dimensions of the structure (right).

The performance of the device can be greatly improved by incorporating a MEMS (Micro-Electro-Mechanical Systems) antenna, where the antenna receiver is a MEMS structure itself, suspended over the substrate. For certain applications, the air gap between the patch and the ground plane can be tuned electrostatically. Not only does this provide better control, it is also possible to obtain sharper antenna response around the resonance frequency of the MEMS structure. FIG. 9 shows the cross-sectional view of a patch antenna suspended over a MEMS resonator. The effective permittivity is modified by the additional dielectric layer (air gap) with height $h_1$ and permittivity $\varepsilon_0$. This is given by $$\varepsilon_{eff} = \frac{\varepsilon_r(h_2 + h_1)}{h_2 + \varepsilon_r h_1}.$$

The resonant frequency of the antenna also changes as it depends on the effective permittivity.

v) MEMS Resonator

A novel feature is the use of a micromechanical resonator (MEMS) to provide the required inductive load to create compact resonant structures. The MEMS resonator is designed to have a resonant frequency at the frequency of operation of the antenna. Furthermore, electrical lengthening is achieved by ensuring the resonator to have an equivalent inductive impedance that matches the antenna impedance. Effectively, this is nothing but a MEMS matching network with the appropriate inductive load.

Electrical lengthening is achieved by choosing the parameters of the piezoelectric resonator for the required equivalent inductance. In terms of materials parameters and dimensions, the equivalent inductance of the mechanical resonator is given by $$L_M = \frac{\rho}{8} \frac{lt}{w} \frac{1}{d_{31}^2 E_p^2}.$$

Since thickness t defines the BAW modes, other resonator dimensions length l and width w can be appropriately chosen. Here, p is density, $d_{31}$ is piezoelectric constant and $E_p$ is the elastic modulus.

Piezoelectric MEMS resonators are perfect for the proposed device, as in the thickness bulk acoustic wave (BAW) mode they can produce resonance frequencies in the gigahertz range: $f_{BAW} = v_s/2t$, where $v_s$ is sound velocity and t is thickness.

Figure 10A:
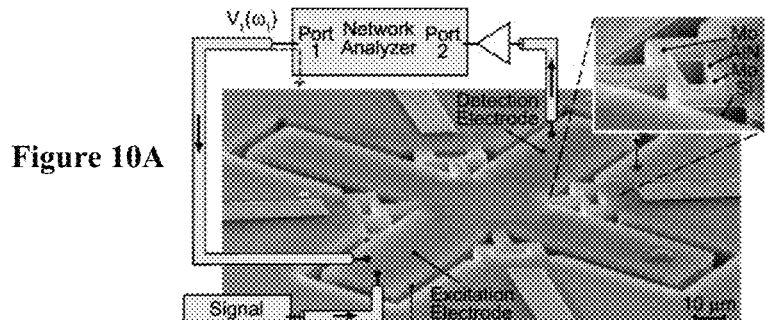
FIGS. 10a and 10B respectively show a scanning electron micrograph of the device and transmission measurement of the device with background removed. The resonator exhibits a wide array of modes.
Figure 10B:
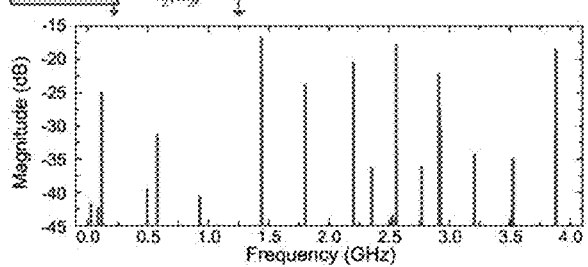

FIG. 10 shows results of a piezoelectric resonator in the shape of a cross-bar with designed soft anchors. This particular resonator comprises single crystal silicon (thickness 10 µm), with molybdenum electrodes (thickness 100 nm) sandwiching an aluminum nitride (AlN) layer (thickness 1 µm) atop the structure for piezoelectric transduction. At the input port, voltage $V_1(\omega_1)$ applied across the AlN excites the structure, and modes with nonzero net strain induce charge at the detection port, resulting in a signal detected via the network analyzer after preamplification. The resonator can comprise intersecting free-free beams of dimensions 150 µm length×25 µm width. As depicted in the transmission measurement, the resonator exhibits a multitude of flexural modes and thickness modes ranging in frequency from 28 MHz to 3.9 GHz.

vi) Rectifier and Filters

Figure 11:
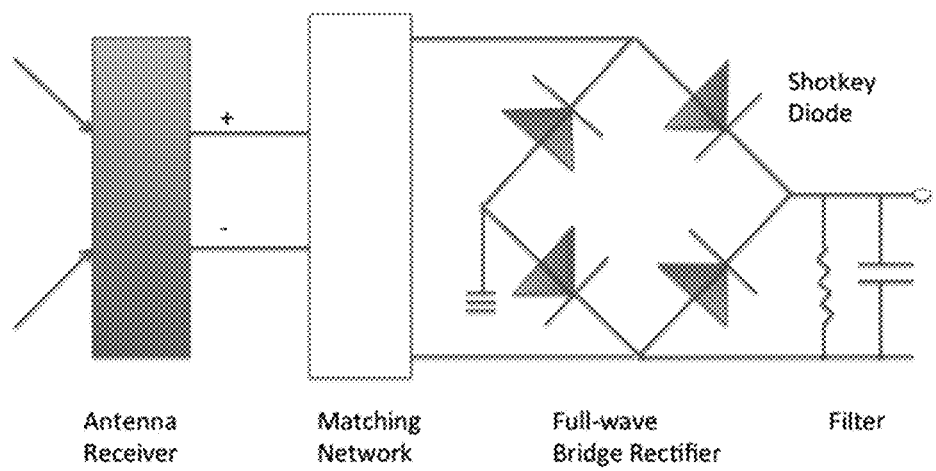
FIG. 11. A standard full-bridge rectifier matched to the receiver antenna output.
Figure 12:
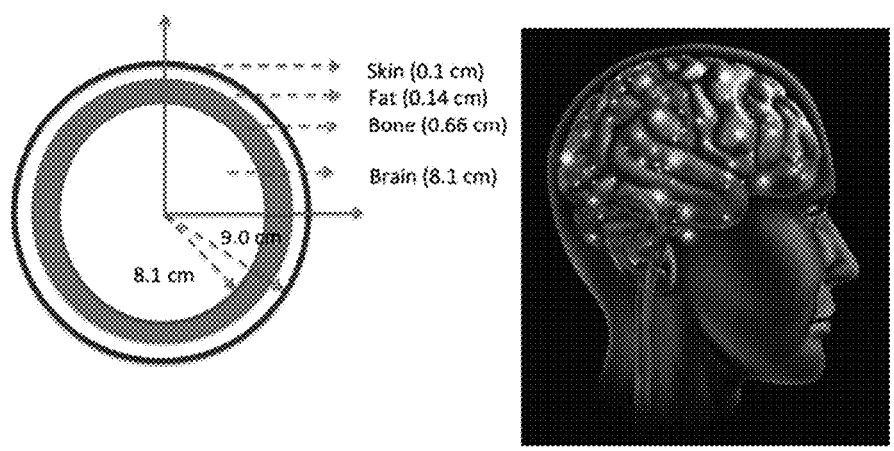
FIG. 12. A model of the human head with four basic layers of tissue materials (left). A schematic figure of the human head (right).

As shown in FIG. 11, the rectifier circuit, including the filters, converts the radiofrequency electromagnetic wave captured by the antenna into DC power. There are several important considerations that must be taken into account in the design and the implementation of the rectifier circuit. First, the rectifier circuit must be a full-wave rectifier, comprising four diodes (and, in some embodiments, consisting of four diodes). Second, the diodes must be of Schotky type to be able to handle high power with ideal operation frequency in the GHz range. Third, the choice of pre-rectifier filters and post-rectifier filters must be validated using simulation. Though, a post-rectifier low-pass filter stage is absolutely necessary, the choice of a pre-rectifier filter stage may have nontrivial effects on efficiency. Since the unwanted harmonics and nonlinear spurious signals may appear at the input stage of the rectifier in a wider band, the bandwidth and the insertion loss of the pre-rectifier stage filter must be carefully chosen.

Modeling, Packaging, Test and Characterization i) Modeling of the receiver circuit: Several receiver (antenna+rectifier) circuit designs is investigated using Agilent ADS software in both time and frequency domains. These designs will be variations of basic design concepts described earlier. Agilent ADS and Microwave Studio (CST) are electronic circuit simulation software that can accurately model circuits in both time and frequency domains. In the time domain, both voltage and current is determined as a function of time at various points of the circuit. In frequency domain, voltage and current is determined as a function of frequency in and around the operation frequency of 2-6 GHz over a predefined bandwidth. In addition, ADS and Microwave Studio contain component libraries from which one can choose the appropriate components for optimal device performance. In addition to providing a complete picture of circuit performance, ADS/Microwave Studio can also reveal non-ideal cases that include reflection, loss, nonlinearity and inter-modulation.

Modeling of propagation through tissue material: Another reference standard simulation tool for modeling full 3D electromagnetic field is ANSYS HFSS (High Frequency Structural Simulator). It allows design and modeling of components such as on-chip embedded passives, interconnects, antennas, IC-packages and RF/microwave components. Finite Difference Time Domain (FDTD) simulations of antenna design is performed using the CST Microwave Studio platform, augmented by ANSYS HFSS and Agilent ADS or Microwave Studio for circuit simulation. More importantly, ANSYS HFSS is used to simulate full 3D propagation of electromagnetic wave in tissue. In addition to the electromagnetic field profiles, ANSYS will be used to simulate SAR (specific absorption rate) and heating profile in tissue material (Human Body Model). SAR is a quantitative measure of power absorbed per unit of mass and time.

ii) Fabrication and Packaging

Fabrication of the device prototypes follows extensive simulation and modeling using Agilent ADS or Microwave Studio (CST) and/or ANSYS HFSS simulation tools. The prototypes is fabricated in two steps: (i) board-level assembly of components and their test and characterization, (ii) Multi-chip module (MCM) assembly as discussed in earlier section.

The antenna module is fabricated by optical lithography using a mask aligner. This includes antenna structure, matching network and microstrip lines. Electrical layers (gold or aluminum) are deposited on a dielectric substrate (either Duroid or highly conductive silicon). The rectifier module contains the Schotky diodes as well as filters. It is possible to obtain a full-wave bridge rectifier for microwave applications in a die form. The rectifier module contains this rectifier and any associated filters.

A biocompatible hermetic package is needed to house the receiver. The two main goals of the package are to provide a hermetic package for the electronics with least interference with the high frequency circuit performance, and to interact as little as possible with the surrounding tissue environment. Ideally, the package material should not have any damaging effects such as inflammation or heating. A number of packaging materials have been extensively studied for use in implanted devices. These include alumina, parlyne, low-temperature co-fired ceramic (LTCC), liquid crystal polymer (LCP) and silicon. LCP may be a good choice as electrodes can be patterned on it using photolithography or sputtering. The antenna chip and the rectifier chip can be bonded using a flip-chip bonding process with anisotropic conductive adhesive. To make electrical contacts between the layers, as discussed earlier, through vias can be created by deep reactive ion etch (DRIE). Though this is the preferred method for packaging, we will explore other options as well.

iii) Test and Characterization—Free Space and Tissue

The wireless power receiver will undergo a number of tests and characterization before being subjected to the final tests where the device will be embedded in a simulated tissue environment or phantom. Here are the planned sequences of tests in free space.

a) Antenna Characterization: Receiver antenna will be characterized through a sequence of tests. A source transmitter antenna (horn type) will be used to transmit power over free space to the receiver antenna. Typical antenna characteristics that will be studied are input impedance, input VSWR (Voltage Standing-Wave Ratio), bandwidth and return loss, and power radiation pattern. Using these measurements, one can obtain directivity, gain and efficiency of the antenna, where efficiency is the power generated at the receiver antenna divided by the input power.

b) Rectifier Characterization: The rectifier circuit (along with filters and matching networks) is characterized by impedance measurements and the DC power generated at the output. Efficiency of the rectifier+antenna circuit is defined by the net DC power generated at the rectifier output divided by the input power transmitted by the transmitter or source antenna. Efficiency is studied as a function of distance in free space.

c) Packaging Characterization: The biocompatible hermetic package is studied for hermeticity by pressure tests with air and water, as tissue density is similar to that of water.

Simulated Tissue Environment (Phantom): Testing of the wireless power receiver in a tissue environment follows the standard practiced in the field of dosimetry, which involves risk evaluation of human exposure to RF fields, e.g., evaluation of SAR, induced field and current density. In addition to the study of effects of unwanted radiation, it also involves characterization of radiation-based therapy and treatment in the radio frequency range. Some of the examples include shortwave diathermy, microwave treatment and magnetic resonance imaging.

Since the wireless power receiver device is intended for biological applications in optogenetics, tests must be performed inside a simulated tissue environment, or a phantom, as shown in FIG. 10. A phantom, a surrogate of a human body, is used for experiments ultimately targeted for human body. For the neurological studies, the phantom must have layers of artificial tissue materials representing the four basic tissue types in the human head: skin, fat, bone and brain. These artificial tissue materials are designed to possess the same electrical characteristics in the frequency range of interest. The figure shows a four-layer schematic of the human head along with the dimensions of the different tissue layers. The basic dimensions and physical parameters of these four layers are given in the table here.

|  | $Kg/m^3$ | cm | $J/kg \cdot K$ |
|---|---|---|---|
| Skin | 1010 | 9.00 | 3662 |
| Fat | 920 | 8.90 | 2378 |
| Bone | 1810 | 8.76 | 1590 |
| Brain | 1040 | 8.10 | 3640 |

The electrical parameters of these four tissue types vary greatly as a function of frequency, as expected. Since the main goal is to maximize power transfer by enabling propagation of electromagnetic wave through these four layers to the wireless power receiver, the fundamental quantities of interest are electrical impedance (needed for impedance matching), wavelength, penetration depth and specific absorption rate (SAR). Calculations and measurements of SAR and heating (temperature increase) due to electromagnetic radiation are needed to ensure that the electromagnetic radiation does not cause unwanted local heating or damage at the cellular level even if the radiation power and frequency are well within the non-ionizing radiation regime.

|  | 2.4 GHz | | | | 5.8 GHz | | |
| --- | --- | --- | --- | --- | --- | --- | --- |
| $\sigma$ (S/m) | $\varepsilon$ | $\lambda$ (mm) | $\delta$ (mm) | $\sigma$ (S/m) | $\varepsilon$ | $\lambda$ (mm) | $\delta$ (mm) |
| Skin | 1.44 | 38 | 20 | 22 | 3.7 | 35.1 | 8.6 | 8.5 |
| Fat | 0.102 | 5.28 | 54 | 119 | 0.29 | 4.95 | 23 | 40 |
| Bone | 0.787 | 18.6 | 28.6 | 29.4 | 2.14 | 15.39 | 12.8 | 9.9 |
| Brain | 1.773 | 48.99 | 17.6 | 21.1 | 4.98 | 44 | 7.6 | 7.1 |

The characteristic depth to which electromagnetic fields penetrate inside the tissue is penetration depth, $\delta=\sqrt{1/\pi\mu\sigma f}$, where $\sigma$ is conductivity, f is frequency and $\mu$ is permeability.

$$SAR = \frac{P}{m} = \sigma\frac{|\vec{E}|^2}{\rho} = C\frac{dT}{dt}\bigg|_{t=0}.$$

Here P is the incident power, m is mass, p is mass density, C is specific heat, T is temperature and t is time. Electrical impedance in tissue $\eta$ is given by $\eta=\eta_0\sqrt{\mu_r/\varepsilon_r}$, where is the $\eta_0$ is free space electrical impedance (377$\Omega$). Using these formulas, one can calculate impedance, SAR, penetration depth and heating. The electrical parameters for two characteristic frequencies of interest are given in the following table.

Figure 13:
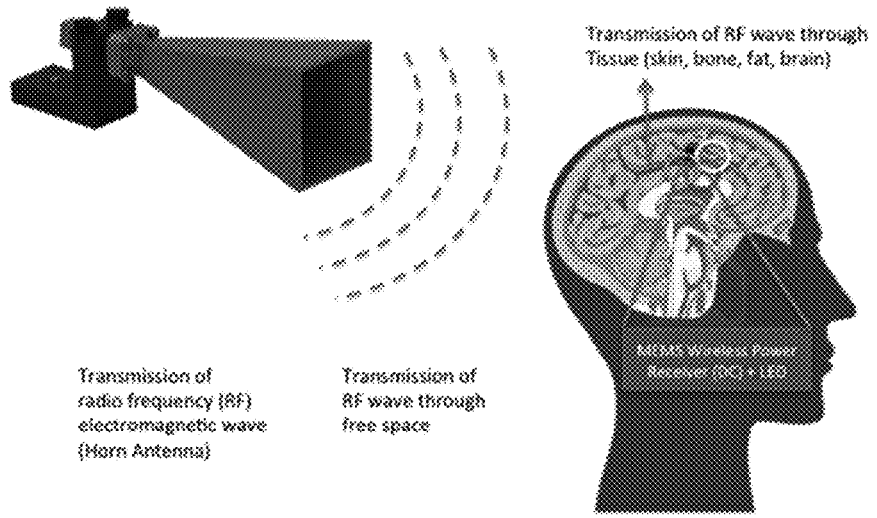
FIG. 13. Testing of the wireless power receiver in a phantom.

As depicted in FIG. 13, the final test is performed with the MEMS receiver embedded inside the brain of the phantom. A horn antenna is used to transmit radio frequency electromagnetic wave. The DC power received at the MEMS wireless receiver is characterized as a function of distance in addition to full characterization of various sub-systems in the receiver such as the receiver antenna, rectifier and packaging.

As shown in FIG. 13, testing of wireless receivers used for diagnostics inside the human body is similar to what is described above. The tissue material composition depends on the location of the implant. Hence, the design of the phantom and the location for testing of the device will depend on the target location of the implant.

The invention claimed is:

1. An implantable device, comprising:
    a wireless patch antenna comprising a planar microstrip radiator and a parallel ground plane separated by a dielectric;
    a resonator configured to receive electromagnetic radiation from the wireless patch antenna wherein the resonator comprises a single crystal silicon layer, an electrode layer and an aluminum nitride layer between the single crystal silicon layer and the electrode layer; and
    a rectifier in electrical communication with the resonator, the rectifier comprising a set of diodes and being configured to convert the electromagnetic radiation to DC power.

2. The device of claim 1, wherein the resonator comprises a transducer to couple to an electromagnetic field of the electromagnetic radiation.

3. The device of claim 1, wherein the wireless patch antenna receives the electromagnetic field of the radiation.

4. The device of claim 1, wherein the resonator comprises the wireless patch antenna patterned on a body of the resonator.

5. The device of claim 1, wherein the wireless patch antenna is electrically or physically coupled to the resonator.

6. The device of claim 1, wherein the resonator is a micromechanical system with dimensions less than 1 mm.

7. The device of claim 1, wherein the resonator is coupled to a capacitor.

8. The device of claim 1, wherein the resonator is connected to a light emitting diode.

9. The device of claim 1, wherein a resonant frequency of the resonator is configured with a frequency of operation of the wireless patch antenna.

10. The device of claim 9, wherein an inductive impedance of the resonator matches an impedance of the wireless patch antenna.

11. The device of claim 10, wherein the resonator is configured to perform electrical lengthening of the electromagnetic radiation.

12. The device of claim 1, further comprising a pre-rectifier filter and a post-rectifier filter.

13. The device of claim 12, wherein the pre-rectifier filter comprises a bandpass filter.

14. The device of claim 12, wherein the post-rectifier filter comprises a low-pass filter.

15. The device of claim 1, wherein the resonator is selected from the group consisting of a micro-electro-mechanical systems (MEMS) resonator, a split-ring resonator (SRR), and a LC resonator.

16. The device of claim 1, wherein the wireless patch antenna comprises a micro-electro-mechanical systems (MEMS) wireless patch antenna.

* * * * *